US006750371B2

(12) United States Patent
Fritz-Langhals et al.

(10) Patent No.: US 6,750,371 B2
(45) Date of Patent: Jun. 15, 2004

(54) PROCESS FOR THE OXIDATION OF ALCOHOLS TO ALDEHYDES AND KETONES IN THE PRESENCE OF NITROXYL COMPOUNDS AS CATALYSTS

(75) Inventors: Elke Fritz-Langhals, Ottobrunn (DE); Juergen Stohrer, Pullach (DE); Hermann Petersen, Burghausen (DE)

(73) Assignee: Consortium fuer elektrochemische Industrie GmbH, Munich (DE)

( * ) Notice: Subject to any disclaimer, the term of this patent is extended or adjusted under 35 U.S.C. 154(b) by 0 days.

(21) Appl. No.: 10/264,682

(22) Filed: Oct. 4, 2002

(65) Prior Publication Data

US 2003/0073871 A1 Apr. 17, 2003

(30) Foreign Application Priority Data

Oct. 11, 2001 (DE) .......................................... 101 50 164
Nov. 15, 2001 (DE) .......................................... 101 56 138

(51) Int. Cl.$^7$ ............................................. C07C 45/29
(52) U.S. Cl. ...................... 568/471; 568/322; 568/361; 568/402
(58) Field of Search ......................... 568/471, 322.361, 568/402

(56) References Cited

U.S. PATENT DOCUMENTS 6,441,243 B1 * 8/2002 Sommerlade et al.
6,451,943 B1 * 9/2002 Burkhardt et al.

FOREIGN PATENT DOCUMENTS

| DE | 40 07 923 A1 | 9/1990 |
| DE | 196 05 039 A1 | 8/1997 |
| DE | 694 15 345 T2 | 12/1998 |
| DE | 100 29 597 A1 | 1/2002 |
| EP | 0 340 703 A1 | 11/1989 |
| EP | 0 801 073 A2 | 10/1997 |
| EP | 0 734 392 B1 | 12/1998 |
| EP | 1 103 537 A1 | 5/2001 |
| WO | WO 01 90111 A1 | 11/2001 |

OTHER PUBLICATIONS

De Luca et al. A Very Mild and Chemoselective Oxidation of Alcohols to Carbonyl Compounds Organic Letters. 2001, vol. 3, No. 19, p. 3041–3043.*

P.L. Anelli et al, *Fast and Selective Oxidation of Primary Alcohols to Aldehydes or Tocarboxylic Acids and of Secondary Alcohols to Ketones Mediated by Oxoammonium Salts Under Two–Phaes Conditions*, Journal of Organic Chemistry, American Chemical Society, Easton, U.S. vol. 52, 1987, pp. 2559–2562.

T. Inokuchi et al., *A Selective and Efficient Method for Alcohol Oxidations Mediated by N–Oxoammonium Salts in Combination with Sodium Bromite*, Journal of Organic Chemistry, American Chemical Society, Easton, U.S., vol. 55, No. 2, 1990, pp. 462–466.

M.J. Verhoef et al., "Studies In Surface Science and Catalysis", vol. 125, p. 465 ff.

D. Brunel et al., "Studies In Surface Science and Catalysis", vol. 125, p. 237 ff.

Miyazawa and Endo, Journal of Polymer Science, Polymer Chemistry Edition 23, 1985, p. 1527 and 2487.

T. Osa, Chem., Lett. 1988, p. 1423

Inokuchi et al., J. Org. Chem. 56, 1991, p. 2416.

English Derwent Abstract AN 2002–217955 [28] Corresponding To De 100 29 597.

English Derwent Abstract AN 1990–298639 [40] Corresponding To DE 40 07 923.

English Derwent Abstract AN 1997–416814 [39] Corresponding To DE 196 05 039.

English Derwent Abstract AN 2001–476952 [52] Corresponding To EP 03 40 703.

A.E.J. de Nooy et al., "On the Use of Stable Organic Nitroxyle Radicals for the Oxidation fo Primary and Secondary Alcohols", 1996, p/ 1153–1174.

Dijksman et al., "Polyamine Immobilised Piperidinyl Oxyl", Synlett 2001, No. 1, p. 102.

P.L. Anelli et al., J. Org. Chem., Vol. 52, 1987, p. 2559.

"Ullmann's Enclopedia Industrial Chemistry", vol. B4.

Cirriminna et al., Chem. Commun. 2000, p. 1441.

Bolm et al., Chem. Commun. 1999, p. 1795.

Bobitt et al., Chem. Commun. 1996, p. 2745.

Miyazawa and Endo, Journal of Molecular Catalysis. 49, 1988, L31.

* cited by examiner

Primary Examiner—Shailendra Kumar
Assistant Examiner—Sikarl A. Witherspoon
(74) Attorney, Agent, or Firm—Brooks Kushman P.C.

(57) ABSTRACT

An alcohol is oxidized to an aldehyde or a ketone in the presence of a nitroxyl compound as catalyst, wherein the alcohol to be oxidized is contained in an organic liquid phase, and is reacted in the presence of a nitroxyl compound with an aqueous phase comprising an oxidant. The reaction is carried out continuously at a contact time of the phases of from 0.1 s to a maximum of 15 minutes, with intensive mixing of the phases. The process produces high yields with low quantities of other oxidation byproducts.

20 Claims, No Drawings

PROCESS FOR THE OXIDATION OF ALCOHOLS TO ALDEHYDES AND KETONES IN THE PRESENCE OF NITROXYL COMPOUNDS AS CATALYSTS

BACKGROUND OF THE INVENTION

1. Field of the Invention

The present invention provides a continuous process for the oxidation of alcohols with the aid of nitroxyl compounds as catalysts in multiphase systems.

2. Background Art

The oxidation of alcohols to aldehydes or ketones is an important transformation in organic chemistry, since compounds having a high reaction potential are formed from readily available alcohols. Such transformations are therefore of great importance in industrial processes. Catalytic processes are particularly advantageous. A process frequently employed in industry is the gas-phase dehydrogenation of alcohols. However, only volatile compounds can be used in this process. The catalyst systems employed are useful with only a few substrates, and the reaction conditions have to be matched specifically to these substrates. Oxidations employing nitroxyl compounds, in particular TEMPO (2,2,6,6-tetramethylpiperidin-1-oxyl) and its derivatives (Review: A. E. J. de Nooy, A. C. Besemer and H. V. Bekkum, SYNTHESIS 1996, 1153), as oxidation catalysts are more generally applicable. Numerous TEMPO derivatives, including TEMPO derivatives on polymeric supports, e.g. polyamine immobilized piperidinyl oxyl "PIPO", Dijksman et al., Synlett 2001, 102, EP 1103537, have been described as oxidation catalysts. These TEMPO-catalyzed oxidations are frequently carried out in two-phase systems, e.g. methylene chloride/water, as disclosed by P. L. Anelli, C. Biffi, F. Montanari and S. Quici, J. Org. Chem. 1987, 52, 2559. The oxidation of alcohols using sodium hypochlorite or sodium hypobromite as oxidant has been studied in detail. Aldehydes can be obtained from primary alcohols, and ketones from secondary alcohols by this process.

When the syntheses are, as is customary, carried out batchwise, the oxidant dissolved in the aqueous phase is added to the organic phase containing the alcohol to be oxidized and the nitroxyl compound. A disadvantage of this existing procedure is that the heat of reaction of the strongly exothermic nitroxyl-catalyzed oxidation process can be removed only with great difficulty, particularly in the case of large batches. This necessitates an increase in the contact time of the two phases and thus the duration of the process, as a result of which secondary reactions, e.g. reaction of alkali-labile groups such as ester group saponification, become significantly more prominent. For the purposes of the present invention, the contact time is the time over which the phases participating in the reaction are mixed.

A further secondary reaction which occurs in batch reactions involves formation of hemiacetals with the starting alcohol and further oxidation to the corresponding ester in accordance with equation 1.

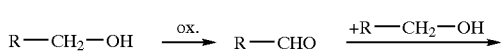

(1)

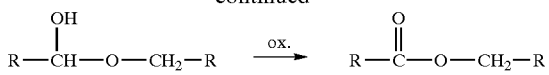

This reaction becomes increasingly prominent with increasing reaction time and phase contact time, so that the achievable yields decrease with increasing batch size, rendering industrial production impossible. A further secondary reaction which decreases the yield of the aldehyde is the further oxidation of the aldehyde to the corresponding carboxylic acid.

For example, the reaction of 20 g of 2-n-butyryloxyethanol formed only 37% of the desired aldehyde together with 12% of 2-n-butyryloxyethyl 2-n-butyryloxyacetate, 4% of butyric acid and 41% of 2-n-butyryloxyacetic acid, as shown in Comparative Example C9 herein. On doubling the batch size, the yield of aldehyde decreased to only 12% and the amount of 2-n-butyryloxyethyl 2-n-butyryloxyacetate was as high as 45% as shown in Comparative Example C10.

EP 0340703 and DE 4007923 describe TEMPO-catalyzed oxidation reactions using sodium hypochlorite solution in a batch reaction. The contact times are more than 15 minutes and particularly more than 30 minutes, since the post-reaction alone required these amounts of time. Although the possibility of carrying out this process continuously was considered, no continuous process was exemplified.

DE 10029597 describes an oxidation process employing a polymer-enlarged TEMPO derivative, likewise as a batch process. The possibility of carrying out the process continuously is envisaged only in conjunction with the use of a membrane reactor, but is not exemplified. Here too, contact times of at least 30 minutes are always employed. DE 69415345 (EP 0734392) employs contact times of 5 hours. In DE 19605039 (EP 0801073), a contact time of at least 45 minutes is employed. In EP 1103537, the after-reaction time alone is 20 minutes. In WO 01/90111, contact times as high as 4 hours were used, and 2 hours were involved with the after-reaction alone.

SUMMARY OF THE INVENTION

It is, therefore, an object of the invention to provide a process for the oxidation of an alcohol to an aldehyde or a ketone in the presence of a nitroxyl compound as catalyst, which process gives higher yields of aldehydes or ketones.

DETAILED DESCRIPTION OF THE PREFERRED EMBODIMENTS

This and other objects are achieved by a process in which the alcohol to be oxidized in an organic liquid phase is reacted in the presence of a nitroxyl compound with an aqueous phase comprising the oxidant, wherein the reaction is carried out continuously at a contact time of the phases of from 0.1 s to a maximum of 15 minutes with intensive mixing of the phases.

It has been surprisingly discovered that simply converting the batch process into a continuous process does not improve the yields. Although no ester formation is then observed, the further oxidation of the aldehyde to the carboxylic acid occurs to an increased extent. The simple conversion of the batch process into a continuous process therefore does not represent a solution to the yield problems. This can also be seen from the Comparative Examples C11 and C12 of the present patent application.

In the process of the invention, the combination of the use of a continuous process together with contact times below 15 minutes is essential. The above-described secondary reactions are suppressed efficiently only by adherence to both process requirements.

The continuous reactors required for the process are known to those skilled in the art. An overview of the most important embodiments are given in, for example, "Ullmann's Encyclopedia of Industrial Chemistry", Vol. B4. The process can be carried out, for example, in continuously operated tube reactors, in continuously operated loop reactors, in continuously operated stirred vessels or cascades of stirred vessels, or by means of centrifugal pumps. In a particularly preferred embodiment, the two phases are combined in a static mixing element and then directed through a tube reactor.

The contact time of the phases is preferably from 1 s to 5 minutes, more preferably from 1 s to 2 minutes, and most preferably from 1 s to 30 s.

Intensive mixing of the phases is preferably achieved by establishing turbulent flow in the reaction mixture. Particular preference is given to turbulent flow at a Reynolds number Re of from 800 to 20,000. Intensive mixing or turbulent flow can be achieved by means of all known mixing systems, e.g. static mixing elements or stirrers. Various mixing systems can also be combined to reach or exceed the Reynolds number.

The organic liquid phase comprises the alcohol and, if desired, one or more organic solvents. Suitable organic solvents include, for example, linear or branched saturated or unsaturated aliphatic hydrocarbons having 1–20 carbon atoms, cyclic aliphatic saturated or unsaturated hydrocarbons having 5–20 carbon atoms or aromatic hydrocarbons having 5–20 carbon atoms, in each of which one or more hydrogen atoms or one or more carbon atoms may be replaced by heteroatoms.

Preference is given to linear or branched saturated or unsaturated aliphatic hydrocarbons having 1–16 carbon atoms, cyclic aliphatic saturated or unsaturated hydrocarbons having 5–16 carbon atoms or aromatic hydrocarbons having 6–16 carbon atoms, in each of which one or more hydrogens may be replaced, independently of one another, by F, Cl, Br, $NO_2$ or CN, or one or more $CH_2$ groups may be replaced, independently of one another, by O, NH, C=O, S, S=O, $SO_2$, P=O, or one or more CH groups may be replaced, independently of one another, by N or P, or quaternary carbons can be replaced by Si.

Examples of suitable organic solvents include hexane, petroleum ether, cyclohexane, decalin, methylene chloride, chloroform, carbon tetrachloride, 1,2-dichloroethane, chlorobenzene, benzene, toluene, 1-chloronaphthalene, ethyl acetate, butyl acetate, ethylene carbonate, tetrahydro-1,3-dimethyl-2(1 H)-pyrimidinone (DMPU), hexamethylphosphortriamide (hexamethylphosphoramide, HMPA), dimethyl sulfoxide (DMSO), diethyl ether, methyl tert-butyl ether, ethylene glycol diethyl ether, diethylene glycol diethyl ether, dioxane, diisopropyl ketone and polydimethylsiloxanes.

The alcohol to be oxidized can be used in concentrations of from 0.1 to 100% by weight based on the organic solution, preferably from 1 to 50% by weight.

For the purposes of the present invention, the term nitroxyl compound encompasses both the oxidized form of the oxoammonium ion and the reduced form of the hydroxylamine, since these forms both occur in the oxidation (A. E. J. de Nooy, A. C. Besemer and H. V. Bekkum, Synthesis 1996, 1155).

The nitroxyl compound used as oxidation catalyst is preferably a di-tert-alkylnitroxyl compound, preferably a nitroxyl compound of the formula I:

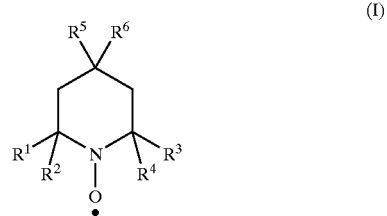

(I)

where the radicals $R^1$, $R^2$, $R^3$ and $R^4$ are each, independently of one another, $C_1$–$C_{12}$-alkyl, $C_2$–$C_{12}$-alkenyl, or $C_6$–$C_{12}$-aryl or aralkyl, and the radicals $R^5$ and $R^6$ each, independently, are hydrogen, OH, CN, halogen, linear or branched, saturated or unsaturated $C_1$–$C_{20}$-alkyl, $C_6$–$C_{20}$-aryl, $C_6$–$C_{20}$-hetaryl or $C_6$–$C_{20}$-aralkyl, $OR^7$, O—$COR^7$, O—$COOR^7$, $OCONHR^7$, COOH, $COR^7$, $COOR^7$, or $CONHR^7$, where $R^7$ is a linear or branched, saturated or unsaturated $C_1$–$C_{20}$-alkyl, $C_6$–$C_{20}$-aryl, $C_3$–$C_{20}$-hetaryl, or $C_6$–$C_{20}$-aralkyl radical, —(O—$CH_2$—$CH_2$)$_n$—$OR^8$, —(O—$C_3H_6$)$_n$—$OR^8$, —(O—($CH_2$)$_4$)$_n$—$OR^8$, or —O—$CH_2$—CHOH—$CH_2$—(O—$CH_2$—$CH_2$—)$_n$—$OR^8$, where $R^8$ is hydrogen, $C_1$–$C_{20}$-alkyl or $C_6$–$C_{20}$-aralkyl, and n=1 to 100, or $CH_2$—CHOH—$CH_3$, $CH_2$—CHOH—$CH_2$—$CH_3$, $NR^9R^{10}$, $NHCOR^9$, $NHCOOR^9$, or $NHCONHR^9$, where $R^9$ and $R^{10}$ are each independently, a linear or branched, saturated or unsaturated $C_1$–$C_{20}$-alkyl, $C_6$–$C_{12}$-cycloalkyl, $C_6$–$C_{20}$-aryl, $C_3$–$C_{20}$-hetaryl, or $C_6$–$C_{20}$-aralkyl radical, where the radicals $R^5$ and $R^6$ may also be joined to form a ring, and the radicals $R^5$ and $R^6$ may in turn be substituted by COOH, OH, $SO_3H$, CN, halogen, primary, secondary or tertiary amino or quaternary ammonium or the radicals $R^5$ and $R^6$ may together constitute =O, =$NR^{11}$, =N—$OR^{11}$, or =N—N=$CR^{11}R^{12}$, where $R^{11}$ and $R^{12}$ are each independently, hydrogen, $C_1$–$C_{20}$-alkyl or $C_6$–$C_{20}$-aralkyl.

Preference is also given to nitroxyl compounds formed from two molecules of the formula I which are linked in the 4 position by a bridge =N—N=. Preference is further given to nitroxyl compounds formed from two or more molecules of the formula I joined to one another via one of the two radicals $R^5$ or $R^6$. Suitable linking groups are, for example, O—alkyl—O, O—$CH_2$-aryl-$CH_2$—O, O—CO—NH-aryl-NH—CO—O, O—CO—NH-alkyl-NH—CO—O and bridges of the formula (O—($CH_2$)$_n$—O)$_m$ where n=2 to 4 and m=2 to 50.

In a further embodiment, the nitroxyl compound is a polymeric structure comprising compounds of the formula I which are linked via the radicals $R^5$ or $R^6$ or $R^5$ and $R^6$. The literature describes many such structures (EP 1103537, Cirriminna et al., Chem. Commun. 2000, 1441; Bolm et al., Chem. Commun. 1999, 1795; Bobbitt et al., Chem. Commun. 1996, 2745, Miyazawa and Endo, J. Molec. Catal. 49, 1988, L31; M. J. Verhoef et al. in "Studies in Surface Science and Catalysis", Vol. 125, p. 465 ff; D. Brunel et al. in "Studies in Surface Science and Catalysis", Vol. 125, p. 237 ff; Miyazawa and Endo, J. POLYMER SCI., Polym. Chem. Ed. 23, 1985, 1527 and 2487; T. Osa, Chem. Lett. 1988, 1423). Examples are PIPO, $SiO_2$-supported TEMPO, and polystyrene- and polyacrylic acid-supported TEMPO.

A particularly preferred nitroxyl compound is a compound of the formula I in which $R^1$, $R^2$, $R^3$ and $R^4$ are each $CH_3$ and $R^5$ and $R^6$ are each, independently, hydrogen, OH, $OR^7$, $O-COR^7$, $O-COOR^7$, or $OCONHR^7$, where $R^7$ is a linear or branched, saturated or unsaturated $C_1-C_{20}$-alkyl radical or a $C_6-C_{20}$-aryl or $C_6-C_{20}$-aralkyl radical, $-(O-CH_2-CH_2)_n-OR^8$, $-(O-C_3H_6)_n-OR^8$, $-(O-(CH_2)_4)_n-OR^8$, or $-O-CH_2-CHOH-CH_2-(O-CH_2-CH_2-)_n-OR^8$, where $R^8$ is hydrogen, $C_1-C_{10}$-alkyl or $C_6-C_{10}$-aralkyl, where n=1 to 100, $CH_2-CHOH-CH_3$, $CH_2-CHOH-CH_2-CH_3$, $NR^9R^{10}$, $NHCOR^{10}$, $NHCOOR^{10}$, or $NHCONHR^{10}$, where $R^9$ and $R^{10}$ are each, independently, hydrogen, a linear or branched, saturated or unsaturated $C_1-C_{20}$-alkyl, $C_6-C_{12}$-cycloalkyl, $C_6-C_{20}$-aryl, or $C_6-C_{20}$-aralkyl radical.

The nitroxyl compound is more preferably a compound of the formula I in which $R^1$, $R^2$, $R^3$ and $R^4$ are each $CH_3$ and $R^5$ and $R^6$ together form a ketal group of the formula $O-CHR^{13}CHR^{14}-O$ or $O-CH_2CR^{15}R^{16}-CH_2-O$, where $R^{13}$, $R^{14}$, $R^{15}$ and $R^{16}$ are each, independently, hydrogen or $C_1-C_3$-alkyl, or the radicals $R^5$ and $R^6$ together represent =O.

The nitroxyl compound is most preferably a compound of the formula I in which $R^1$, $R^2$, $R^3$ and $R^4$ are each $CH_3$, $R^5$ is hydrogen, and $R^6$ is hydrogen, OH, $OR^7$, or $O-COR^7$, where $R^7$ is a linear or branched saturated $C_1-C_{12}$-alkyl radical or an aryl or benzyl radical, $-(O-CH_2-CH_2)_n-OR^8$, $-(O-C_3H_6)_n-OR^8$, $-(O-(CH_2)_4)_n-OR^8$, or $-O-CH_2-CHOH-CH_2-(O-CH_2-CH_2-)_n-OR^8$, where n=1 to 50 and $R^8$ is hydrogen, $CH_2-CHOH-CH_3$, or $CH_2-CHOH-CH_2-CH_3$, $NR^9R^{10}$, or $NHCOR^{10}$, where $R^9$ and $R^{10}$ are each, independently, a linear or branched saturated $C_1-C_{12}$-alkyl radical or an aryl or benzyl radical.

Examples of nitroxyl compounds which can be used are TEMPO, 4-hydroxy-TEMPO, 4-oxo-TEMPO, 4-amino-TEMPO, 4-acetamido-TEMPO, 4-benzoyloxy-TEMPO, 4-acetoxy-TEMPO, and PIPO.

The nitroxyl compound is preferably used in an amount of from 0.01 to 50 mol %, most preferably in an amount of from 0.1 to 20 mol %, based on the amount of alcohol to be oxidized. It can be used as a solution in the organic phase or in the aqueous phase or in supported form as a separate phase.

As oxidant, use is made of a compound selected from the group consisting of chlorine, bromine, iodine, hypochlorite, chlorite, chlorate, hypobromite, bromite, bromate, hypoiodite, iodite, iodate, periodate, $Fe(CN)_6^{3-}$, N-chloro compounds, and mixtures thereof. Preferred oxidants are hypochlorite and hypobromite. In the case of salt-like oxidants, preference is given to those having sodium, potassium, calcium, ammonium, or tetra-alkylammonium counterions.

The oxidant can also be generated in situ, e.g. electrochemically; by hydrolysis, e.g. by hydrolysis of N-chloro compounds; or by redox reactions, for example hypochlorite or hypobromite solutions obtained by disproportionation of chlorine or bromine in alkaline solution or the redox reaction between hypochlorite and bromide which leads to the formation of hypobromite.

The oxidants employed are preferably used in concentrations of from 0.1 M to their respective saturation concentration.

Further possible additives are halogens, e.g. bromine, and salts, e.g. alkali metal, alkaline earth metal or ammonium halides or sulfates, carbonates, hydrogencarbonates, phosphoric acid and its alkali metal, alkaline earth metal or ammonium salts or carbon dioxide. These additives can in each case be added to one of the two phases, if desired in solution, or may be added in dissolved form as third component to the continuous process.

In oxidations using hypochlorite, the addition of bromine or bromide in amounts of from 0.01 to 100 mol %, based on the amount of hypochlorite used, is preferred. Particular preference is given to adding bromine or bromide in amounts of from 1 to 50 mol %.

The pH of the aqueous phase is preferably in the range from 6 to 14, most preferably from 7 to 12. The desired pH is preferably established by addition of a buffer, e.g. sodium hydrogencarbonate, disodium hydrogenphosphate or sodium dihydrogenphosphate, by addition of an acid, e.g. carbon dioxide, phosphoric acid, hydrochloric acid or sulfuric acid, or a base, e.g. NaOH.

The reaction temperature is preferably from −10 to +80° C., most preferably from −5° C. to +30° C.

Preferred alcohols for the oxidation are all primary and secondary alcohols which have a miscibility gap with the aqueous phase, the miscibility gap established, if necessary, by addition of an organic solvent.

Primary alcohols are oxidized to aldehydes and secondary alcohols to ketones. In the case of compounds which contain both primary and secondary hydroxy groups, the primary hydroxy groups are preferentially oxidized. An overview of the order of reactivity when a plurality of hydroxy groups are present is given by A. E. J. de Nooy, A. C. Besemer and H. V. Bekkum, Synthesis 1996, 1153.

The alcohols to be oxidized are preferably linear or branched saturated or unsaturated aliphatic alcohols having 1–60 carbon atoms, cyclic aliphatic saturated or unsaturated alcohols having 5–60 carbon atoms or alcohols having 6–60 carbon atoms which are substituted by an aromatic radical, in each of which one or more hydrogen atoms or one or more carbon atoms may be replaced by heteroatoms.

Particular preference is given to linear or branched saturated or unsaturated aliphatic alcohols having 1–30 carbon atoms, cyclic aliphatic saturated or unsaturated alcohols having 5–30 carbon atoms or alcohols having 6–30 carbon atoms which are substituted by an aromatic radical, in each of which one or more hydrogen atoms may be replaced, independently of one another, by F, Cl, Br, I, $NO_2$, ONO, CN, NC, or SCN, one or more $CH_2$ groups may be replaced, independently of one another, by O, NH, C=O, $CO_2$, S, S=O, $SO_2$, P=O, $PO_2$, or an acetylenic $C_2$ unit, one or more CH groups may be replaced, independently of one another, by N, B or P, and quaternary carbons may be replaced by Si, Sn or Pb.

Great preference is given to linear or branched saturated or unsaturated aliphatic alcohols having 1–30 carbon atoms, cyclic aliphatic saturated or unsaturated alcohols having 5–30 carbon atoms, or alcohols having 6–30 carbon atoms which are substituted by an aromatic radical, in each of which one or more hydrogen atoms may be replaced, independently of one another, by F, Cl, Br, I, $NO_2$, ONO, CN, NC, or SCN, one or more $CH_2$ groups may be replaced, independently of one another, by O, NH, C=O, $CO_2$, S, S=O, $SO_2$, P=O, $PO_2$ or an acetylenic $C_2$ unit, one or more CH groups may be replaced, independently of one another, by N, B or P, and quaternary carbon atoms may be replaced by Si, Sn or Pb, where at least one of these substituents is present in the 2 or 3 position relative to the carbon atom bearing the hydroxy group.

Great preference is likewise given to alcohols whose partition ratio between the organic phase and the aqueous phase is at least 80:20.

Preferably, the following types of hydroxy compounds are oxidized: 2- and 3-hydroxycarboxylic esters, 2- and 3-hydroxy-carboxamides, 2-hydroxylalkyl carboxylates, N-(2-hydroxyalkyl)carboxamides, 1- or 2-hydroxyketones or dihydroxyketones, hydroxymethyl or hydroxyethyl epoxides, O-alkyl-O'-2-hydroxyalkyl carbonates, bis(2-hydroxyalkyl) carbonates, 2- and 3-hydroxylactones, hydroxy-1,3-dioxolanes, hydroxy-1,3-dioxanes, hydroxy-1,4-dioxanes, 2- and 3-hydroxyimides, 2- and 3-hydroxyalkylimides, 2- and 3-hydroxylactams, 2- and 3-hydroxyalkylurethanes, 2-hydroxy ethers, 2,2'-dihydroxy ethers of oligoethylene glycols, oligopropylene glycols, 2-hydroxyalkyl alkylsulfonates or arylsulfonates, alkyl 2-hydroxyalkylsulfonates, 2-aminoalcohols, 2-trialkylsilylalcohols and 2-trialkylsilyloxyalcohols.

Examples of the above-mentioned classes of compounds are: 2-hydroxyethyl isobutyrate, 3-hydroxypropyl isobutyrate, 2,2-dimethyl-4-hydroxymethyl-1,3-dioxolane, cyclohexylideneglycerol, pantolactone, dihydroxyacetone, glycerol, 1,4-butanediol, trimethylsilylethanol, tert-butyldimethylsilyloxyethanol, and phthalimidoethanol.

2-n-Butyryloxyacetaldehyde was obtained from 2-hydroxyethyl butyrate in an 80 percent yield at 100% conversion by means of the process of the invention.

The process of the invention likewise makes it possible to synthesize unstable substances such as trimethylsilylacetaldehyde whose preparation has previously been unsuccessful.

The following examples serve to illustrate the invention, but do not serve to limit its scope in any way.

EXAMPLE 1

2-n-Butyryloxyacetaldehyde

The following solutions were prepared:

Solution 1: 700 g (5.30 mol) of 2-n-butyryloxyethanol, 43 g (0.28 mol) of TEMPO and 47.0 g (0.294 mol) of bromine in 10 l of methylene chloride.

Solution 2: 4.20 l of sodium hypochlorite solution (technical-grade) was brought to a pH of 9.5 by means of gaseous $CO_2$. Concentration: about 1.7 M.

The solutions 1 and 2 were pumped by means of metering pumps from two reservoirs (volume in each case 10 l) via a static mixing element into a helically wound 50 m long V4A tube (internal diameter: 2 mm, external diameter: 3.2 mm) cooled in an ice bath. The pumping rate was 133 ml/min for solution 1 and 55 ml/min for solution 2. Sampling after 25 meters indicated complete conversion. The reaction mixture was collected in a 20 l container, the methylene chloride solution was drained off, washed with 0.5 l of 10 percent strength HCl, 0.5 l of 10 percent strength sodium thiosulfate solution, and 0.5 l of water, and fractionally distilled. Yield: 70% of 2-n-butyryloxyacetaldehyde.

EXAMPLE 2

2-n-Butyryloxyacetaldehyde

The following solutions were prepared:

Solution 1: 494 g (3.74 mol) of 2-n-butyryloxyethanol and 35.4 g (0.205 mol) of 4-hydroxy-TEMPO in 7.27 l of methylene chloride.

Solution 2: 4.20 l of sodium hypochlorite solution (technical-grade) was brought to a pH of 9.5 by means of gaseous $CO_2$. Concentration: about 2.1 M.

Solution 3: 84.9 g of NaBr in 313 ml of water.

The solutions 1, 2 and 3 were pumped from reservoirs by means of metering pumps via a static mixing element into a helically wound 20 m long titanium tube (internal diameter: 3 mm, external diameter: 4.1 mm) cooled in an ice bath. The pumping rate was 48 l/h for solution 1, 13 l/h for solution 2 and 0.5 l/h for solution 3. The reaction mixture was collected in a 20 l container, the methylene chloride solution was drained off, washed with 0.5 l of 10 percent strength HCl, 0.5 l of 10 percent strength sodium thiosulfate solution and 0.5 l of water and fractionally distilled. Yield: 80% of 2-n-butyryloxyacetaldehyde.

EXAMPLE 3

2-n-Butyryloxyacetaldehyde

The experiment was carried out as described in example 2. The pH of the sodium hypochlorite solution was set to 11. Yield: 81% of 2-n-butyryloxy-acetaldehyde.

EXAMPLE 4

2-n-Butoxyacetaldehyde 2-n-Butoxyethanol was reacted as in example 2. Yield: 80%, b.p.: 40° C. (12 mbar).

EXAMPLE 5

Pivalaldehyde

Neopentyl alcohol was reacted as in example 2. Solution 1 consisted of 363 g of neopentyl alcohol and 48 g of 4-acetamido-TEMPO in 1 l of methylene chloride. The pumping rate was 30 l/h for solution 1, 22 l/h for solution 2 and 0.5 l/h for solution 3. Yield: 93% ($^1$H-NMR standard analysis).

EXAMPLE 6

Trimethylsilylacetaldehyde 2-(Trimethylsilyl)ethanol was reacted as in example 2. Yield in solution: 71% ($^1$H-NMR standard analysis). $^1$H-NMR ($CDCl_3/CH_2Cl_2$): δ=0.48 (s, 3 $CH_3$), 2.30 (s, $CH_2$), 9.67 (s, CHO); storage at room temperature leads to slow decomposition of the substance.

EXAMPLE 7 tert-Butyldimethylsilyloxyacetaldehyde 2-(tert-Butyldimethylsilyloxy)ethanol was reacted as in example 2.

Solution 1 consisted of 108 g (0.610 mol) of 2-(tert-butyldimethylsilyloxy)ethanol and 5.8 g of 4-hydroxy-TEMPO in 400 ml of ethyl acetate. Flow rates: 48 l/h for solution 1, 30 l/h for solution 2. tert-Butyldimethylsilyloxyacetaldehyde was isolated by fractional distillation of the ethyl acetate phase. B.p.: 74–80° C. (22 mbar).

EXAMPLE 8

N-(2-Oxoethyl)phthalimide

The preparation from N-(2-hydroxyethyl)phthalimide was carried out as in example 2; cooling was carried out by means of tap water. Yield: 74%, m.p. 114° C. (from methylene chloride).

EXAMPLE C9

2-n-Butyryloxyacetaldehyde (Comparative Example)

20.0 g (151 mmol) of 2-n-butyryloxyethanol were dissolved in 300 ml of methylene chloride and admixed with 1.30 g (8.32 mmol) of TEMPO. The solution was cooled to −10° C. and a solution of 2.0 g (16.8 mmol) of KBr in 9 ml of water was added. 150 g (278 mmol) of technical-grade sodium hypochlorite solution whose pH had been adjusted to about 9.5 by means of solid sodium hydrogencarbonate was then introduced over a period of one hour while stirring vigorously and cooling. The temperature was maintained at about 0° C. during the addition. After the addition, the phases were separated and the organic phase was washed in succession with 15 ml of 10 percent strength HCl, 15 ml of 10 percent strength sodium thiosulfate solution and 15 ml of water. $^1$H-NMR standard analysis indicated a yield of 37% of 2-isobutyroxyacetaldehyde in the dichloromethane phase in this batch process. The following further products were likewise found: 12% of 2-n-butyryloxyethyl 2-n-butyryloxyacetate (methylene chloride phase), 8% of 2-n-butyryloxyacetic acid (methylene chloride phase), 33% of 2-n-butyryloxy-acetic acid (aqueous phase), 4% of butyric acid (aqueous phase).

EXAMPLE C10

2-n-Butyryloxyacetaldehyde (Comparative Example)

40.0 g (303 mmol) of 2-n-butyryloxyethanol were reacted and worked up by a method analogous to example 9. The reaction time was 100 minutes. $^1$H-NMR standard analysis indicated a yield of 20% of 2-n-butyryloxyacetaldehyde, 45% of 2-n-butyryloxyethyl 2-n-butyryloxyacetate, 22% of 2-n-butyryloxyacetic acid and 8% of butyric acid in the methylene chloride phase of this continuous process.

EXAMPLE C11

2-n-Butyryloxyacetaldehyde (Comparative Example)

The solutions 1 and 2 from Example 1 were employed.

The two solutions were synchronously mixed in a volume ratio of 2.4:1 in a residence vessel (V=250 ml) stirred at high speed. The mean residence time was set to 20 minutes by simultaneously draining off the solution. Yield of n-butyryloxyacetaldehyde in methylene chloride: 19%, unreacted alcohol: 15%, n-butyryloxyacetic acid: 32% (method: GC and $^1$H-NMR standard analysis).

EXAMPLE C12

Pivalaldehyde (Comparative Example)

Neopentyl alcohol was reacted by a method analogous to Example 11. The solutions 1 and 2 from Example 5 served as the reactants. Yield of pivalaldehyde: 47%, unreacted alcohol: 25% (method: GC and $^1$H-NMR standard analysis).

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for the oxidation of an alcohol to an aldehyde or a ketone in the presence of a nitroxyl compound as catalyst, comprising oxidizing the alcohol in an organic liquid phase in the presence of a nitroxyl compound and an aqueous phase comprising an oxidant, wherein the reaction is carried out continuously at a contact time of the phases of from 0.1 s to a maximum of 15 minutes with intensive mixing of the phases, separating the organic liquid phase from the aqueous phase at a time defining the end of the contact time, and separating said aldehyde or ketone from the organic liquid phase.

2. The process of claim 1, wherein the contact time of the phases is from 1 s to 5 minutes.

3. The process of claim 1, wherein the contact time of the phases is from 1 s to 2 minutes.

4. The process of claim 1, wherein intensive mixing is achieved by establishing turbulent flow.

5. The process of claim 4, wherein the turbulent flow has a Reynolds number Re of from 800 to 20,000.

6. The process of claim 1, wherein the organic liquid phase comprises the alcohol to be oxidized and optionally, one or more organic solvents.

7. The process of claim 1, wherein the alcohol to be oxidized is used in a concentration of from 0.1 to 100% by weight based on the weight of the organic solution.

8. The process of claim 1, wherein the nitroxyl compound is a di-tert-alkylnitroxyl compound.

9. The process of claim 8, wherein the nitroxyl compound is a compound of the formula I,

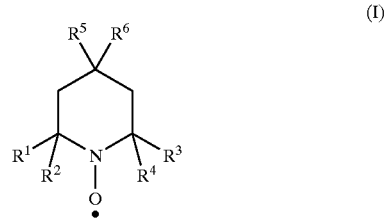

(I)

where the radicals $R^1$, $R^2$, $R^3$ and $R^4$ are each independently $C_1$–$C_{12}$-alkyl, $C_2$–$C_{12}$-alkenyl, or $C_6$–$C_{12}$-aryl or aralkyl, and the radicals $R^5$ and $R^6$ each independently are hydrogen, OH, CN, halogen, linear or branched, saturated or unsaturated $C_1$–$C_{20}$-alkyl, $C_6$–$C_{20}$-aryl, $C_6$–$C_{20}$-hetaryl, $C_6$–$C_{20}$-aralkyl, OR$^7$, O—COR$^7$, O—COOR$^7$, OCONHR$^7$, COOH, COR$^7$, COOR$^7$, or CONHR$^7$, where $R^7$ is a linear or branched, saturated or unsaturated $C_1$–$C_{20}$-alkyl, $C_6$–$C_{20}$-aryl, $C_3$–$C_{20}$-hetaryl, or $C_6$–$C_{20}$-aralkyl radical, —(O—CH$_2$—CH$_2$)$_n$—OR$^8$, —(O—C$_3$H$_6$)$_n$—OR$^8$, —(O—(CH$_2$)$_4$)$_n$—OR$^8$, or —O—CH$_2$—CHOH—CH$_2$—(O—CH$_2$—CH$_2$—)$_n$—OR$^8$, where $R^8$ is hydrogen, $C_1$–$C_{20}$-alkyl, $C_6$–$C_{20}$-aralkyl and n=1 to 100, CH$_2$—CHOH—CH$_3$, CH$_2$—CHOH—CH$_2$—CH$_3$, NR$^9$R$^{10}$, NHCOR$^9$, NHCOOR$^9$, or NHCONHR$^9$, where $R^9$ and $R^{10}$ are each independently a linear branched, saturated or unsaturated $C_1$–$C_{20}$-alkyl, $C_6$–$C_{12}$-cycloalkyl, $C_6$–$C_{20}$-aryl, $C_3$–$C_{20}$-hetaryl, or $C_6$–$C_{20}$-aralkyl radical, where the radicals $R^5$ and $R^6$ may also be joined to form a ring, the radicals $R^5$ and $R^6$ may be substituted by COCH, OH, SO$_3$H, CN, halogen, primary, secondary or tertiary amino or quaternary ammonium, or the radicals $R^5$ and $R^6$ may together also represent =O, =NR$^{11}$, =N—OR$^{11}$, =N—N=CR$^{11}$R$^{12}$, where $R^{11}$ and $R^{12}$ are each independently hydrogen, $C_1$–$C_{20}$-alkyl or $C_6$–$C_{20}$-aralkyl.

10. The process of claim 9, wherein two molecules of the formula I are linked in the 4-position by a =N—N= bridge.

11. The process of claim 1, wherein the nitroxyl compound is employed in an amount of from 0.01 to 50 mol % based on the amount of alcohol to be oxidized.

12. The process of claim 1, wherein the nitroxyl compound is employed in an amount of from 0.1 to 20 mol %, based on the amount of alcohol to be oxidized.

13. The process of claim 1, wherein the oxidant comprises compounds selected from the group consisting of chlorine, bromine, iodine, hypochlorite, chlorite, chlorate, hypobromite, bromite, bromate, hypoiodite, iodite, iodate, periodate, $Fe(CN)_6^{3-}$, N-chloro compounds, and mixtures thereof.

14. The process of claim 1, wherein the reaction carried out takes place at a temperature of from −10 to +80° C.

15. The process of claim 1, wherein the reaction carried out takes place at a temperature of from −5° C. to +30° C.

16. The process of claim 1, where the oxidation takes place in a tubular reactor.

17. The process of claim 16, wherein the tubular reactor is preceded by a static mixer.

18. A process for the oxidation of an alcohol to an aldehyde or a ketone in the presence of a nitroxyl compound as catalyst, comprising oxidizing the alcohol in an organic liquid phase in the presence of a nitroxyl compound and an aqueous phase comprising an oxidant, wherein the reaction is carried out continuously at a contact time of the phases of from 0.1 s to a maximum of 15 minutes with intensive mixing of the phases, separating the organic liquid phase from the aqueous phase at a time defining the end of the contact time, and separating said aldehyde or ketone from the organic Liquid phase, wherein the nitroxyl compound is a compound of the formula I,

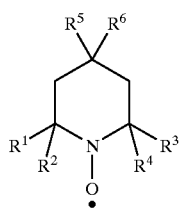

(I)

where the radicals $R^1$, $R^2$, $R^3$ and $R^4$ are each independently $C_1$–$C_{12}$-alkyl, $C_2$–$C_{12}$-alkenyl, or $C_6$–$C_{12}$-aryl or aralkyl, and the radicals $R^5$ and $R^6$ each independently are hydrogen, OH, CN, halogen, linear or branched, saturated or unsaturated $C_1$–$C_{20}$-alkyl, $C_6$–$C_{20}$-aryl, $C_6$–$C_{20}$-hetaryl, $C_6$–$C_{20}$-aralkyl, O—$COR^7$, O—$COOR^7$, $OCONHR^7$, COOH, $COR^7$, $COOR^7$, or $CONHR^7$, where $R^7$ is a linear or branched, saturated or unsaturated $C_1$–$C_{20}$-alkyl, $C_6$–$C_{20}$-aryl, $C_3$–$C_{20}$-hetaryl, or $C_6$–$C_{20}$-aralkyl radical, —(O—$CH_2$—$CH_2$)$_n$—$OR^8$, —(O—$C_3H_6$)$_n$—$OR^8$, —(O—$(CH_2)_4$)$_n$—$OR^8$, or —O—$CH_2$—CHOH—$CH_2$—(O—$CH_2$—$CH_2$—)$_n$—$OR^8$, where $R^8$ is hydrogen, $C_1$–$C_{20}$-alkyl, $C_6$–$C_{20}$-aralkyl and n=1 to 100, $CH_2$—CHOH—$CH_3$, $CH_2$—CHOH—$CH_2$—$CH_3$, $NR^9R^{10}$, $NHCOR^9$, $NHCOOR^9$, or $NHCONHR^9$, where $R^9$ and $R^{10}$ are each independently a linear branched, saturated or unsaturated $C_1$–$C_{20}$-alkyl, $C_6$–$C_{12}$-cycloalkyl, $C_6$–$C_{20}$-aryl, $C_3$–$C_{20}$-hetaryl, or $C_6$–$C_{20}$-aralkyl radical, where the radicals $R^5$ and $R^6$ may also be joined to form a ring, the radicals $R^5$ and $R^6$ may be substituted by COOH, OH, $SO_3H$, CN, halogen, primary, secondary or tertiary amino or quaternary ammonium, or the radicals $R^5$ and $R^6$ may together also represent =O, =$NR^{11}$, =N—$OR^{11}$, =N—N=$CR^{11}R^{12}$, where $R^{11}$ and $R^{12}$ are each independently hydrogen, $C_1$–$C_{20}$-alkyl or $C_6$–$C_{20}$-aralkyl.

19. The process of claim 18 wherein the contact time is from 1 s to 2 minutes.

20. The process of claim 18, wherein said nitroxyl compound is selected from the group consisting of TEMPO, 4-hydroxy-TEMPO, 4-oxo-TEMPO, 4-amino-TEMPO, 4-acetamido-TEMPO, and mixtures thereof.

* * * * *